(12) United States Patent
Højgaard

(10) Patent No.: US 10,143,657 B2
(45) Date of Patent: Dec. 4, 2018

(54) SOLID ORAL DOSAGE FORM OF IRINOTECAN FOR THE TREATMENT OF CANCER

(71) Applicant: ONCORAL PHARMA APS, Ballerup (DK)

(72) Inventor: Bent Højgaard, Allerod (DK)

(73) Assignee: Oncoral Pharma ApS, Copenhagen (DK)

( * ) Notice: Subject to any disclaimer, the term of this patent is extended or adjusted under 35 U.S.C. 154(b) by 9 days.

(21) Appl. No.: 15/112,157

(22) PCT Filed: Jan. 16, 2015

(86) PCT No.: PCT/EP2015/050728
§ 371 (c)(1),
(2) Date: Jul. 15, 2016

(87) PCT Pub. No.: WO2015/107131
PCT Pub. Date: Jul. 23, 2015

(65) Prior Publication Data
US 2016/0331692 A1  Nov. 17, 2016

(30) Foreign Application Priority Data

Jan. 17, 2014  (EP) .................................... 14151688

(51) Int. Cl.
| | |
|---|---|
| *A61K 9/28* | (2006.01) |
| *A61K 9/20* | (2006.01) |
| *A61K 9/48* | (2006.01) |
| *C07D 491/22* | (2006.01) |
| *A61K 31/4745* | (2006.01) |

(52) U.S. Cl.
CPC .......... *A61K 9/2886* (2013.01); *A61K 9/2013* (2013.01); *A61K 9/2018* (2013.01); *A61K 9/2031* (2013.01); *A61K 9/2054* (2013.01); *A61K 9/282* (2013.01); *A61K 9/284* (2013.01); *A61K 9/2853* (2013.01); *A61K 9/2893* (2013.01); *A61K 9/4825* (2013.01); *A61K 9/4833* (2013.01); *A61K 9/4858* (2013.01); *A61K 9/4866* (2013.01); *A61K 9/4891* (2013.01); *A61K 31/4745* (2013.01); *C07D 491/22* (2013.01)

(58) Field of Classification Search
None
See application file for complete search history.

(56) References Cited

U.S. PATENT DOCUMENTS

| | | | | |
|---|---|---|---|---|
| 6,569,452 | B1 * | 5/2003 | Civaroli ............... | A61K 9/4816 424/451 |
| 2002/0147208 | A1 | 10/2002 | Fleshner-Barak | |
| 2003/0215523 | A1 * | 11/2003 | Ozawa ................ | C07D 209/30 424/649 |
| 2003/0236236 | A1 * | 12/2003 | Chen .................... | A61K 31/566 514/171 |
| 2004/0009225 | A1 * | 1/2004 | Vanderbist ........... | A61K 9/4858 424/484 |
| 2007/0053869 | A1 * | 3/2007 | Sugiyama ............ | A61K 9/4858 424/78.38 |

FOREIGN PATENT DOCUMENTS

| | | |
|---|---|---|
| WO | 0050007 A1 | 8/2000 |
| WO | 0110443 A1 | 2/2001 |
| WO | 0130351 A1 | 5/2001 |
| WO | 09098469 A1 | 8/2009 |

OTHER PUBLICATIONS

US Pharmacopeia. Pharmaceutical Dosage Forms—Capsules, pp. 1-3 [online]. US Pharmacopeia, available online from Nov. 27, 2010 [retrieved on Feb. 10, 2017]. Retrieved from the internet<http://web.archive.org/web/20101127093056/http://pharmacopeia.cn/v29240/usp29nf24s0_c1151s22.html>.*
Allegrini et al. (2008) "A pharmacokinetic and pharmacodynamic study on metronomic irinotecan in metastatic colorectal cancer patients", Br. J Cancer 98:1312-1319.
Berlin et al. (2001) "Phase I safety, pharmacokinetic (PK), and bioavailability {F}study of a semi-solid matrix {SSM} formulation of oral Irinotecan. in patients with advanced solid tumors", Proc Am Soc Clin Oncol 130:Abstr 521.
Chabot (1997) "Clinical Pharmacokinetics of Irinotecan" Clin. Pharmacokinet., 33 (4): 245-259.

(Continued)

*Primary Examiner* — Katherine Peebles
(74) *Attorney, Agent, or Firm* — Agris & von Natzmer, LLP; Cheryl H Agris

(57) ABSTRACT

The present invention relates to a composition, in particular a solid pharmaceutical composition comprising a compound having the formula I, as a free base or a salt thereof, and a mixture comprising a vehicle and a non-ionic surfactant in an amount sufficient to achieve solubilization of compound (I); and typically wherein the composition is coated with an enteric coating. Such composition is particularly useful in treatment of cancer.

19 Claims, No Drawings

(56) References Cited

OTHER PUBLICATIONS

Dumez et al. (2006) "A phase I dose-finding clinical pharmacokinetic study of an oral formulation of irinotecan (CPT-11) administered for 5 days every 3 weeks in patients with advanced solid tumours", Annals of Oncology 17:1158-1165.

Furman et al. (2006) "Cefixime Allows Greater Dose Escalation of Oral Irinotecan: A Phase I Study in Pediatric Patients With Refractory Solid Tumors", J Clin Oncol 24:563-570.

Goff et al. (2012) "Phase I study of oral irinotecan as a single-agent and given sequentially with capecitabine", Invest New Drugs 30:290-298.

Kuppens et al. (2004) "Topoisomerase I Inhibitors in the Treatment of Gastrointestinal Cancer: From Intravenous to Oral Administration", Clin.I Colorec. Cancer 4(3):163-180.

Kuppens et al. (2006) "Dose-Finding Phase I Clinical and Pharmacokinetic Study of Orally Administered Irinotecan in Patients with Advanced Solid Tumors", Clin Cancer research 12; 3774-3781.

Moiseyenko et al. (2010) (2010) "Phase II study of metronomic chemotherapy (MC) with irinotecan (CPT-11) in patients with refractory metastatic colorectal cancer (MCRC)" J. Clin. Oncol., ASCO Annual Meeting Proceedings. 28; No. 15 suppl., Abstract e14109.

Perez et al. (2004) "Randomized Phase II Study of Two Irinotecan Schedule for Patients With Metastatic Breast Cancer Refractory to an Anthracycline, a Taxane, or Both", J Clin Oncol 22; 2849-2855.

Pitot HC et al. (2006) "A phase I and pharmacokinetic study of a powder-filled capsule formulation of oral irinotecan (CPT-11) given daily for 5 days every 3 weeks in patients with advanced solid tumors", Cancer Chemother Pharmacol 58:165-172.

Radomski et al. (2000) "Phase I and Pharmacokinetic Study of Oral Irinotecan in Pediatric Patients with Solid Tumors" Proc Am Soc Oncol 19: Abstr. 2329.

Rea et al. (2005) "A phase I/II and pharmacokinetic study of irinotecan in combination with capecitabine as first-line therapy for advanced colorectal cancer", Annals of Oncology; 16: 1123-1132.

Schoemaker et al. (2001) A Phase 1 and Pharmacokinetic (PK) Trial of Oral formulation of Irinotecan Administered Daily for 14 days Every 3 Weeks in Patients (pts) with Solid Tumors, Proc. Am Soc Clin Oncol 20:75.

Sharma S et al. (2001) "A Phase I and Pharmacokinetic Study of Powder-filled Capsule Formulation of Oral Irinotecan (CPT-11) Given Daily for 14 Days Every 3 Weeks in Patients with Advanced Solid Tumors", Proc Am Soc Oncol 103a; Poster Abstr. 407.

Soepenberg et al. (2005) "Phase I Pharmacokinetic, Food Effect, and Pharmacogenetic Study of Oral Irinotecan Given as Semisolid Matrix Capsules in Patients with Solid Tumors", Clin Cancer Res 11; 1504-1511.

International Search Report for Counterpart PCT Appln No. PCT/EP2015/050728, dated Feb. 18, 2015.

International Preliminary Report on Patentability for Counterpart PCT Appln No. PCT/EP2015/050728, dated Jul. 19, 2016.

EP Office Action for EP counterpart appln. EP15700474.8 dated Apr. 24, 2017.

Response to EP Office Action for EP counterpart appln. EP15700474.8 dated May 15, 2017.

* cited by examiner

SOLID ORAL DOSAGE FORM OF IRINOTECAN FOR THE TREATMENT OF CANCER

FIELD OF THE INVENTION

This present invention relates to a pharmaceutical composition comprising Irinotecan (or a pharmaceutically acceptable salt thereof) and intended for oral use for the treatment of cancer. Typically, the oral dosage form is a solid dosage form that has a high oral bioavailability of Irinotecan and at the same time a low variability in absorption compared to prior tested oral formulations of Irinotecan. This invention also relates to the preparation of a stable solid oral dosage form and methods of use thereof, for instance in the treatment of cancer. Typically the composition is administered orally in combination with 5 fluorouracil (5-FU) or with capecitabine being the oral pro-drug of 5-FU. The oral formulation is intended for use in patients with metastatic colorectal carcinoma (mCRC), metastatic breast cancer (mBC) or other cancer indication responsive to irinotecan antitumor activity.

BACKGROUND OF THE INVENTION

Irinotecan (7-ethyl-10-[4-(1-piperidino)-1-piperidino]-carbonyloxycamptothecin) is a semisynthetic analogue of the natural alkaloid camptothecin extracted from plants such as *Camptotheca acuminata*. Irinotecan is an antineoplastic agent of the topoisomerase I inhibitor class and used in the treatment of various types of cancer like metastatic colorectal cancer (mCRC), non-small cell lung cancer (NSCLC) and triple negative breast cancer. Irinotecan is a precursor for and is in the body converted by carboxylesterase enzymes primarily in the liver to the active metabolite SN-38. SN-38 is approximately 100-1000 times more cytotoxic than irinotecan in human and rodent tumor cell lines. In vitro irinotecan displays cytotoxic activity in tumor cells with $IC_{50}$ values for irinotecan in the range 1.6 to 24 mg/L while those of SN-38 are in the range 2 to 14 µg/L as given by Chabot R G [1]. Irinotecan and its active metabolite SN-38 bind to the topoisomerase I-DNA complex and prevent the DNA from unwinding. Since topoisomerase I complexes with DNA only during DNA synthesis, the cytotoxic action of the irinotecan metabolite likely takes place during S-phase. The formation of a topoisomerase I/camptothecin/DNA-cleavable complex results in cell injury or death.

Irinotecan is currently only administered as an aqueous solution for intravenous infusion over 30-90 minutes weekly or every 3rd week. The product is originally marketed as an infusion concentrate under the trade names CAMPTOSAR® or CAMPTO® and in the form of irinotecan, hydrochloride trihydrate (a salt of the irinotecan base).

A solid oral dosage form like a tablet formulation could provide significant convenience benefit to the patients, who today have to attend the clinics or hospitals at repetitive visits over longer period to receive their intravenous chemotherapy medication. Development of an oral product for home treatment will prevent the patient from being tied up to an infusor at the hospital a thus significantly improve the quality of life for patients who need to undergo multiple cycles of treatment. From a pharmaco-economic perspective, outpatient treatment will offer the society a significant reduction in health care costs to treat the individual patient, if the patient can take his medication at home.

In addition, the availability of an oral treatment will make alternative dosing schedules such as more frequent dosing with a smaller dose much more feasible. By more frequent dosing, the cancer cells will have prolonged exposure to the cell cycle specific action of irinotecan improving the anti-tumor activity. At a lower but more frequent dose, the side effects may be reduced while maintaining the same or better efficiency on tumor cells by targeting more cells in the active S-phase. A more frequent dosing regimen of irinotecan was shown to have a significant benefit both in terms of lower toxicity for the host and in efficacy in terms of time to progression and overall survival for patient treated with irinotecan [2; 3; 4]. Metronomic dosing or dose dense therapy, i.e. giving the chemotherapy at regular intervals at a low dose is a relative new concept within chemotherapy that was pioneered e.g. by Robet Kerble from the University of Toronto [5].

Several attempts have been made in order to prepare oral formulations of irinotecan as described by Kuppens et al [6]. All of these efforts have been based on the Irinotecan, hydrochloride, trihydrate salt. Initial human phase I oral studies were performed using the intravenous product. The product was orally administered together with juice for masking of the bitter taste and for prevention of nausea upon intake [7; 8; 9]. More easily used oral formulations included 5, 20 and 50 mg powder-filled capsules [10; 11; 12; 13]. Also 5, 20 and 50 mg semi-solid matrix capsules for extended release of irinotecan were attempted [14; 15; 16; 17]. Clinical phase I studies using these formulations show that oral administration of irinotecan is feasible and may have favorable pharmacokinetic characteristics. The oral bioavailability of irinotecan was however very variable and low as found by Berlin et al. [15] and Radomski et al. [8].

Irinotecan is used as first-line therapy in patients with metastatic carcinoma of the colon or rectum in combination with 5-fluorouracil in a treatment regimen abbreviated "FOLFIRI". The most significant adverse effects and dose-limiting factor of Irinotecan is severe diarrhea and extreme suppression of the immune system. Irinotecan is further used in combination with capecitabine (Xeloda®) being an orally active 5-FU analogue. This analogue in combination with irinotecan was well tolerated and more convenient than irinotecan and 5-FU intravenous combinations in patients with previously untreated advanced colorectal cancer in a phase I/II clinical trial, see Rea D W et al. A solid oral dosage form of irinotecan offers the possibility for an all tablet based dose regimen "CAPIRI" of the "FOLFIRI" treatment due to the presence of capecitabine as an oral tablet formulation of 5-FU.

REFERENCES

1. Chabot R G.: Pharmacokinet., 33 (4): 245-259 (1997)
2. Moiseyenko, V et al.: Journal of Clinical Oncology, ASCO Annual Meeting Proceedings. 28; No. 15 suppl., Abstract e14109 (2010)
3. Allegrini G et al.: Br. J Cancer 98; 1312-1319 (2008)
4. Perez E A et al.: J Clin Oncol 22; 2849-2855 (2004)
5. Carmen Phillips: NCI Cancer Bulletin, Jun. 27, 2006, Volume 3/Number 26.
6. Kuppens et al.: Clinical Colorectal Cancer 4(3): 163-180 (2004)
7. Drengler R L et al: J. Clin Oncol 17; 685-696 (1999)
8. Radomski et al: Proc Am Soc Oncol 19; Abstr. 2329 ((2000)
9. Furman et al: J Clin Oncol 24; 563-570 (2006)
10. Dumez et al. Annals of Oncology 17; 1158-1165, (2006)

11. Pitot H C et al. Cancer Chemother Pharmacol 58; 165-172 (2006)
12. Sharma S et al. Proc Am Soc Oncol 103a; Poster Abstr. 407 (2001)
13. Schoemaker er al. Proc. Am Soc Clin Oncol 20; 75a, (2001)
14. Goff et al. Invest New Drugs 30; 290-298 (2012)
15. Berlin et al. Proc Am Soc Clin Oncol 130; Abstr 521 (2001)
16. Kuppens et al. Clin Cancer research 12; 3774-3781 (2006)
17. Soepenberg et al. Clin Cancer Res 11; 1504-1511 (2005)
18. Rea D W et al. Annals of Oncology; 16: 1123-1132 (2005).

SUMMARY OF THE INVENTION

The present inventors have realized that a combination of a mixture of vehicle and non-ionic surfactant wherein irinotecan is solubilized and processed into a solid composition which is then enteric coated achieves a high oral bioavailability of irinotecan and at the same time a low variability in absorption in a mammal, in particular a human subject and thereby making it appropriate as drug product of the narrow index drug irinotecan. The pharmaceutical compositions of the present invention may, upon oral administration to a human subject, exhibit a bioavailability (as measured by area under the curve, AUC) of at least 8%, such as at least 10% or at least 15% of that observed following intravenous administration of an equivalent dosage of irinotecan (e.g., CAMPTOSAR® (U.S. FDA NDA No. 020571) when measured under the same conditions.

Accordingly, the present invention relates to a solid composition comprising a compound of formula (I)

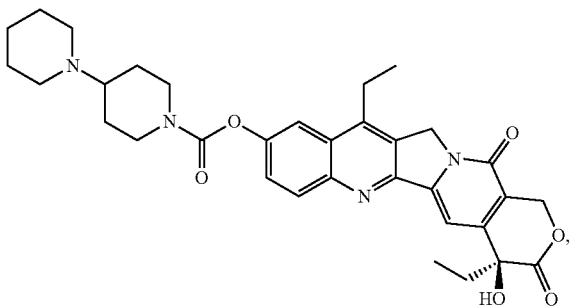 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant. Preferably, the composition is coated with an enteric coating. Typically, the composition is a pharmaceutical composition.

The compound of formula (I) as used herein is intended to cover any form whether on crystalline or amorphous form, and is intended to cover the free base as well as salts thereof, including a pharmaceutically acceptable salt. When on crystalline form the compound (I) may be on anhydrous as well as hydrous form. Thus, the "compound of formula (I)" or "compound (I)" used interchangeably herein, encompass all such forms of compound (I) as well as salts or base thereof. The pharmaceutically acceptable salt is an acid addition salt.

In another aspect the present invention concerns a solid composition, such as a pharmaceutical composition, comprising a compound of formula (I)

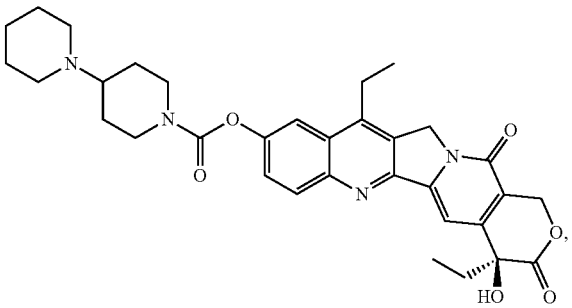 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant, for use in treatment of a cancer in a mammal in need thereof. Preferably, the composition is coated with an enteric coating. Typically, the cancer is selected from metastatic colorectal carcinoma, metastatic breast cancer (mBC), and Non-small cellular lung cancer (NSCLC).

In a further aspect the present invention concerns a method of treating a cancer in a mammal, e.g. a human subject, in need thereof, comprising administration of a solid composition, such as a pharmaceutical composition, comprising a compound of formula (I)

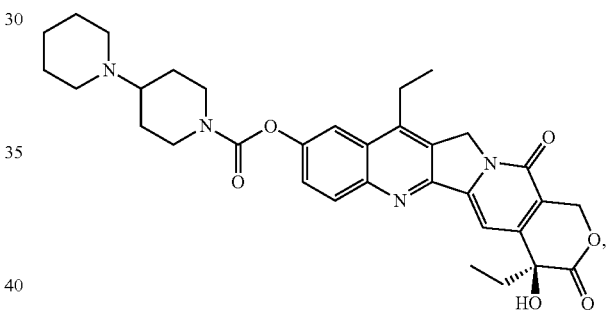

as a free base or a salt thereof, wherein the compound (I) is solubilized in a mixture comprising a vehicle and a non-ionic surfactant. Preferably, the composition is coated with an enteric coating.

In a further aspect the present invention concerns a method of preparing a solid composition, such as a pharmaceutical composition, comprising a compound of formula (I)

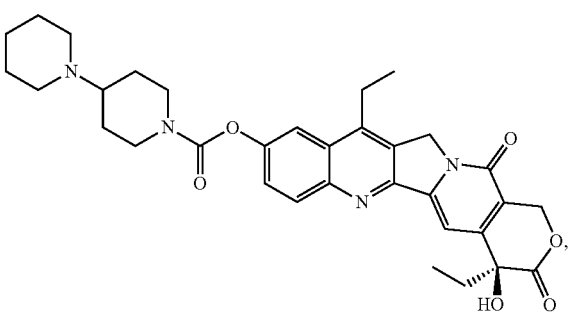 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant characterized by the steps of (a) solubilizing the compound of formula I as a free base or a salt thereof in a mixture comprising a vehicle and a non-ionic surfactant, (b) preparing the solid composition comprising the compound (I) solubilized in the mixture comprising the vehicle and the non-ionic surfactant, and (c) optionally coating the composition with an enteric coating. Preferably, the composition is coated with an enteric coating.

Further objects and advantages of the present invention will appear from the following description, and claims.

DESCRIPTION OF THE INVENTION

The present invention relates to a solid composition comprising a compound of formula I

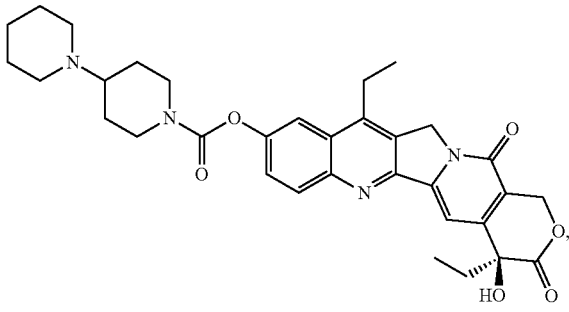 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant. The compound of formula (I) has the systematic chemical name: (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. In Chemical Abstract (CAS) the chemical name is: [1,4'-Bipiperidine]-1'-carboxylicacid,(4S)-4,11-diethyl-3,4,12,14-tetrahydro-4-hydroxy-3,14-dioxo-1H-pyrano[3',4':6,7]indolizino[1,2-b]quinolin-9-yl ester. Typically, the solid composition is a pharmaceutical composition.

As used herein the term "solubilized" means that the compound of formula (I) as the free base or a salt thereof is encompassed in the mixture of the vehicle and the non-ionic surfactant that makes the compound more soluble in water compared to the compound it selves. In general, solubilized means as described in: International Union of Pure and Applied Chemistry, "Compendium of Chemical Terminology" ("the Gold Book"), 2nd edition. Blackwell Scientific Publications, Oxford, 1997.

In a further embodiment the compound of formula I is the free base. For instance, the free base is anhydrous or is a hydrate, preferably anhydrous.

In a still further embodiment the compound of formula I is a salt. Typically, the salt is a pharmaceutically acceptable salt, such as the hydrochloride salt. For instance, the salt is anhydrous or is a hydrate, preferably a tri-hydrate.

In order to achieve a high oral bioavailability of irinotecan and at the same time a low variability in absorption in a mammal the composition is coated with an enteric coating. In relation to the free base of compound (I) a composition without an enteric coating will provide high oral bioavailability of irinotecan, and is believed also to provide a low variability in absorption in a mammal Whereas when a salt of compound (I) is used the enteric coating will provide a low variability in absorption in a mammal.

When the compound (I) is the free base a typical mixture comprising the vehicle and the non-ionic surfactant comprises a saturated or unsaturated medium or long chain fatty acid component as the vehicle and a water-soluble surfactant with a Hydrophile-Lipophile Balance (HLB) value above 9 as the non-ionic surfactant.

When the compound (I) is the salt, such as the HCl salt, a typical mixture comprising the vehicle and the non-ionic surfactant comprises a polyethylene glycol component as the vehicle and a water-soluble surfactant with a Hydrophile-Lipophile Balance (HLB) value above 9 as the non-ionic surfactant.

Typically, the water-soluble surfactant is selected from Vitamin E polyethylene glycol succinate, Polysorbate 80, Polyoxyl 40 hydrogenated castor oil, Polyoxyl 35 castor oil, Caprylocaproyl macrogolglycerides, Polyoxyl 15 Hydroxystearate, Polyoxyethylene 10 oleoyl ether, a pegylated tocopherol (e.g., tocopherol polyethylene glycol succinate derivative, such as a vitamin E TPGS), a poloxamer, wherein useful poloxamers (also denoted polyoxypropylene-polyoxyethylene block copolymers) include, for example, poloxamer 188, poloxamer 237, poloxamer 338, poloxamer 407, and other block copolymers of ethylene oxide and propylene oxide such as the Pluronic® and/or Tetronic™ series available from BASF Corporation of Florham Park, N.J. Suitable block copolymers of the Pluronic™ series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic™ F38, P65, P68LF, P75, F77, P84, P85, F87, F88, F98, P103, P104, P105, F108, P123, F123, F127, 10R8, 17R8, 25R5, and 25R8. Suitable block copolymers of the Tetronic™ series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

In some instances, the vehicle and the non-ionic surfactant may be selected from one component being both a vehicle and a non-ionic surfactant. Typically, such component is Lauroyl polyoxylglycerides.

The solid composition of the present invention is enteric coated when the compound (I) is a salt, and optionally enteric coated when the compound (I) is the free base. In one embodiment the enteric coating is insoluble in gastric juice and in intestinal juice below a predetermined pH in a human subject, but soluble in intestinal juice above the predetermined pH in the human subject. Such predetermined pH is preferably selected in a range from about 4.5 to about 7, such as from about 5 to about 6.5, typically, the predetermined pH may be about 5.5.

Typically, the composition of the present invention comprises from about 0.5% to about 50% by weight of the compound (I) (based on 100% total weight of the composition without the enteric coating), such as from about 2% to about 30% by weight of the compound (I), such as from about 2% to about 15% by weight of the compound (I), such as from about 2% to about 8% by weight of the compound (I). When the compound (I) is the free base it is preferred that the composition of the present invention comprises from about 3% to about 8%, such as from about 3% to about 5%, by weight of the compound (I). When the compound (I) is the salt, typically the HCl salt, it is preferred that the composition of the present invention comprises from about 4% to about 8%, such as from about 4% to about 6%, by weight of the compound (I).

The composition of the present invention comprises the compound (I) in an amount of from 0.5 mg to about 150 mg (calculated based on the content of the free base of the compound (I)). In a further embodiment, the compound (I) is present in an amount from about 1 to about 100 mg, for example, the compound (I) is present in an amount from about 2 mg to about 80 mg, from about 4 mg to about 70 mg, or from about 25 mg to about 60 mg. Typically, the compound (I) is present in an amount of about 60 mg, about 30 mg, about 15 mg, or about 7.5 mg.

In a further embodiment the vehicle is selected from a saturated or unsaturated medium or long chain fatty acid. Preferably, the saturated or unsaturated medium or long chain fatty acid contains from 8 to 24 carbon atoms, such as from 8 to 20 carbon atoms, such as from 16 to 18 carbon atoms.

In a still further embodiment the vehicle is selected from a saturated or unsaturated medium chain fatty acid. Typically, the medium chain fatty acid contains from 8-12 carbon atoms, such as caprylic acid (C8), capric acid (C10) or lauric acid (C12).

In a further embodiment the vehicle is selected from a saturated or unsaturated long chain fatty acid. Typically, the long chain fatty acid contains from 14-24 carbon atoms, such as linoleic acid (18:2), oleic acid (18:1), palmitic acid (16:0), Palmitoleic acid (C16:1), linoleic acid (18:3), and stearic acid (18:0), and mixtures thereof, wherein the first number in the brackets refers to the number of carbon atoms in the fatty acid chain, and the second number refers to the degree of unsaturation.

In a still further embodiment the vehicle is selected from a polyethylene glycol (PEG). Typically, the PEG is selected from a PEG having an average molecular weight of at least 1000, for example, at least 3000, at least 4000, or at least 6000, such as from 1500 to 35000, e.g. from 8000 to 20000, preferably the PEG is PEG 6000.

In a further embodiment the vehicle is selected from a mixture of a saturated or unsaturated medium or long chain fatty acid and a polyethylene glycol (PEG).

When the vehicle is selected from a PEG, it is typically present in an amount from about 20 to about 60 w/w %, such as from about 25 to about 50 w/w % or about 25 to about 40 w/w %, such as about 25 w/w % based on the total weight of the composition without the enteric coating. Typically, PEG is present in an amount from about 20 to about 30 w/w % when PEG and poloxamer is mixed, such as about 25 w/w %, or from about 30 to about 40 w/w % when PEG and TPGS is mixed, such as 37 w/w %.

In a still further embodiment the non-ionic surfactant is selected from a poloxamer and a pegylated tocopherol.

When the non-ionic surfactant is selected from a pegylated tocopherol it is typically selected from a tocopherol polyethylene glycol succinate derivative, such as a Vitamin E Polyethylene Glycol Succinate.

When the non-ionic surfactant is selected from a poloxamer it is typically selected from poloxamer 188, poloxamer 237, poloxamer 338, poloxamer 407, and other block copolymers of ethylene oxide and propylene oxide such as the Pluronic® and/or Tetronic™ series available from BASF Corporation of Florham Park, N.J., such as poloxamer 188.

When the non-ionic surfactant is selected from a poloxamer it is typically present in an amount from about 0.5 to about 25 w/w %, such as from about 5 to about 20 w/w % or about 10 to about 20 w/w % (based on 100% total weight of the composition without the enteric coating).

In a further embodiment the mixture of the vehicle and the surfactant is a mixture of PEG and a hydrophilic polymeric surfactant. Typically, such surfactant is a poloxamer. The PEG and the hydrophilic polymeric surfactant are typically present in a proportion (on a weight/weight basis) of from about 1:3 to about 10:1, from about 1:1 to about 5:1, from about 3:2 to about 4:1 or from about 2:1 to about 3:1, such as in a proportion of about 3:2 (on a weight/weight basis). Preferably, the PEG is selected from PEG 6000 and the hydrophilic polymeric surfactant is selected from poloxamer 188 at a weight ratio of from about 2:1 to about 3:1, such as from about 2:1 to about 2.5:1, such as about 3:2.

In a still further embodiment the mixture of the surfactant and the vehicle is a mixture of a pegylated tocopherol and a long chain fatty acid, for example palmitic acid. Typically the long chain fatty acid, for example palmitic acid, and pegylated tocopherol present in the proportion (on a weight/weight basis) of from about 1:3 to about 10:1 from about 1:1 to about 5:1, from about 3:2 to about 4:1 or from about 2:1 to about 3:1, such as in a proportion of about 5.5:1 (on a weight/weight basis). In one embodiment the long chain fatty acid is palmitic acid and the pegylated tocopherol is vitamin E TPGS at a weight ratio of about 2:1 to about 3:1, such as from about 2:1 to about 2.5:1, such as about 5.5:1.

In another embodiment the mixture of the vehicle and the surfactant is a mixture of a PEG and a pegylated tocopherol, such as a mixture of PEG 6000 and vitamin E TPGS at a weight ratio from 6:4 to about 20:1, such as from about 3:1 to 10:1, such as about 5.5:1.

When the composition of the present invention is a pharmaceutical composition it may contain further excipients in accordance with common general practice within formulation of solid pharmaceuticals. Thus, the solid pharmaceutical composition of the present invention may further comprise one or more pharmaceutically acceptable excipients. Examples of such excipients include, but are not limited to, fillers, diluents, binders, lubricants, glidants, enhancers, wetting agents, surfactants, antioxidants, metal scavengers, pH-adjusting agents, acidifying agents, alkalizing agents, preservatives, buffering agents, chelating agents, stabilizing agents, coloring agents, complexing agents, emulsifying and/or solubilizing agents, absorption enhancing agents, modify release agents, flavoring agents, taste-masking agents, humectants, and sweetening agents. Each of these excipients constitutes individual embodiments and may be added to any of the claims in any suitable combination.

Examples of suitable fillers, diluents and/or binders include lactose (e.g. spray-dried lactose, α-lactose, β-lactose, Tabletose®, various grades of Pharmatose®, Microtose® or Fast-Floc), microcrystalline cellulose (various grades of Avicel®, Elcema®, Vivacel®, Ming Tai® or Solka-Floc), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, and collagen.

Examples of metal scavengers include, but are not limited to, tartaric acid, citric acid, oxalic acid, EDTA and salts thereof, and DPTA (diethylenetriaminepentaacetic acid) and salts thereof.

Examples of diluents include, but are not limited to, calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, and sugar.

Examples of binders include, but are not limited to, acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, and pregelatinized starch.

Examples of glidants and lubricants include, but are not limited to, stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of antioxidants include, but are not limited to, ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, and TPGS or other tocopherol derivatives. The concentration of an antioxidant and/or a stabilizing agent in the tablet may be, for example, from about 0.1% w/w to about 5% w/w (based upon 100% total weight of the unloaded tablet).

Typically, the composition of the present invention is a solid composition comprising a solid core and an enteric coating and such solid core is typically selected from any one of a tablet core, capsule core, pellet core or granulate core. In an embodiment the pharmaceutical composition of the present invention is selected from a tablet. In another embodiment the pharmaceutical composition of the present invention is selected from a capsule. In a further embodiment the pharmaceutical composition of the present invention is selected from a pellet. In a still further embodiment the pharmaceutical composition of the present invention is selected from a granulate.

Preparation of the pharmaceutical compositions can be achieved by different processes known to the skilled person. The key process step is formation of the granules, which contain the active ingredient in solubilized or dispersed form. The granulates can be produced by different granulation processes to achieve the provided formulations, for instance high shear mixing, spray granulation, spray drying, hot melt extrusion and casting followed by milling: The mixture of vehicles and surfactants is melted (at typically 75° C.) and butylated hydroxytoluene is added. The active ingredient (irinotecan base or irinotecan hydrochloride) is then added to the vehicle mixture and dissolved (irinotecan base) or dispersed (irinotecan hydrochloride). Lactose monohydrate was transferred to the granulation equipment to serve as carrier for the vehicle. The molten active vehicle is then slowly poured or sprayed upon the lactose monohydrate to form granules while cooling. For hot melt extrusion, the process will be different as all excipients are mixed, heated and extruded.

The produced granules are mixed with extra-granular excipients for 10 minutes and next lubricant is added and mixed for five minutes. The mixture can be the compressed to tablets or filled into hard shell capsules.

When the pharmaceutical composition is a tablet the solid tablet core is typically a compressed or molded tablet having a hardness of from about 20 N to about 150 N.

In a still further embodiment of the present invention the mixture is loaded into the solid core. Typically, the compound of formula I is dissolved in the mixture and loaded into the solid core.

In a further embodiment the pharmaceutical composition of the present invention may upon dispersion in 900 ml 0.5M phosphate buffer at pH=8.0 dissolve the compound (I) so more than 1.5 times of the compound (I) is found in solution compared to the dispersed compound (I) alone after 60 to 180 minutes.

In a still further embodiment the pharmaceutical composition of the present invention may upon dispersion in 900 ml 0.5M phosphate buffer at pH=8.0 dissolve the compound (I) so more than 2.0 times of the compound (I) is found in solution compared to the dispersed compound (I) alone after 60 to 180 minutes.

In a further aspect the present invention concerns a composition comprising a compound of formula I

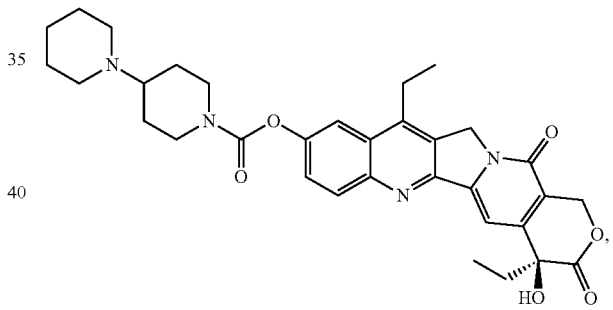

as a free base or a salt thereof, wherein the compound (I) is solubilized in a mixture comprising a vehicle and a non-ionic surfactant for use in treatment of cancer in a mammal in need thereof. Preferably, the composition is coated with an enteric coating. In further embodiments the cancer is selected from metastatic colorectal carcinoma, metastatic breast cancer (mBC), Non small cellular lung cancer (NSCLC) or other cancer indication responsive to irinotecan antitumor activity. In a still further embodiment the composition is administered daily for at least 5 doses of 5 mg/m$^2$ to 200 mg/m$^2$ within a treatment cycle. In a further embodiment the composition is administered every second day for at least 5 doses of 5 mg/m$^2$ to 200 mg/m$^2$ within a treatment cycle. In a still further embodiment the composition is administered once or twice daily. Typically, the daily dosage is from 5 to 200 mg/m$^2$, such as from 10 to 150 mg/m$^2$, e.g. such as from 30 to 100 mg/m$^2$.

In a still further aspect the present invention relates to a method of treating a cancer in a mammal in need thereof, comprising administration of a composition comprising a compound of formula I

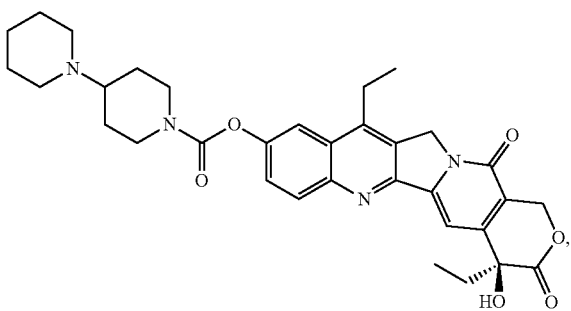 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant. The cancer is preferably selected from metastatic colorectal carcinoma, metastatic breast cancer (mBC), Non-small cellular lung cancer (NSCLC) or other cancer indication responsive to irinotecan antitumor activity.

In an embodiment the present invention relates to a method of treating a cancer in a mammal in need thereof, comprising administration of the composition of any one of the embodiments herein, wherein the composition is administered daily or every second day for at least 5 doses of 5 mg/m$^2$ to 200 mg/m$^2$ within a treatment cycle. In a further embodiment the composition is administered once or twice daily. Typically, the daily dosage is from 5 to 200 mg/m$^2$, such as from 10 to 150 mg/m$^2$, e.g. such as from 30 to 100 mg/m$^2$.

In a further aspect the present invention relates to a method of reducing immunosuppressing side effects of irinotecan cancer treatment of a mammal in need thereof, comprising administration of the composition of any one of the embodiments herein, wherein the composition is administered daily or every second day for at least 5 doses of 5 mg/m$^2$ to 200 mg/m$^2$ within a treatment cycle. In a further embodiment the composition is administered once or twice daily. Typically, the daily dosage is from 5 to 200 mg/m$^2$, such as from 10 to 150 mg/m$^2$, e.g. such as from 30 to 100 mg/m$^2$.

In a further aspect the present invention relates to a method of preparing a composition comprising a compound of formula I

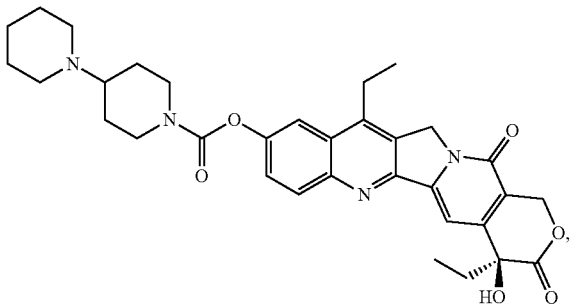 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound (I) is solubilized in a mixture comprising a vehicle and a non-ionic surfactant; and wherein the composition is optionally coated with an enteric coating characterized by the steps of (a) solubilizing the compound of formula I as a free base or a salt thereof in a mixture comprising a vehicle and a non-ionic surfactant, (b) preparing the solid composition comprising the compound (I) solubilized in the mixture comprising the vehicle and the non-ionic surfactant as a granulate, and optionally compressing the granulate to a tablet or filling a capsule with the granulate, and (c) optionally coating the composition with an enteric coating. Preferably, the composition is coated with an enteric coating.

Definitions

The term "acid addition salt" is intended to include "pharmaceutically acceptable acid addition salt" which indicates salts which are not harmful to the patient. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 66, 2, (1977) which is incorporated herein by reference.

The term "HLB" or "HLB value" of a surfactant refers to the Hydrophilic-Lipophilic Balance and is a measure of the degree to which it is hydrophilic or lipophilic, determined by calculating values for the different regions of the molecule. For non ionin surfactants the HLB=20*Mh/M, where M is the molecular mass of the whole molecule and Mh is the molecular mass of the hydrophilic portion of the Molecule. An HLB value of 0 corresponds to a completely lipidphilic/hydrophobic molecule, and a value of 20 corresponds to a completely hydrophilic/lypidphobic molecule.

The term "mammal" or "mammal subject" as used herein (are interchangeable) refers to all sorts of mammals, such as humans, horses, pigs, dogs, cats, sheeps, etc.

As used herein an "enteric coating" is a barrier applied to oral medication that controls the location in the digestive system where it is absorbed. Most enteric coatings work by presenting a surface that is stable at the highly acidic pH found in the stomach, but breaks down rapidly at a less acidic (relatively more basic) pH. For example, they will not dissolve in the acidic juices of the stomach (pH ~3), but they will in the alkaline (pH 7-9) environment present in the small intestine. Materials used for enteric coatings include fatty acids, waxes, shellac, plastics, and plant fibers. Sometimes the abbreviation "EC" is added beside the name of the drug to indicate that it has an enteric coating Typically the Composition of coatings is methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, Sodium alginate and stearic acid.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of de-scribing the invention are to be construed to cover both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

EXAMPLES

Further description of the present invention will now be done by the following non-limiting examples. It should be kept clearly in mind that the examples are merely illustrative of the present invention and should not be construed as limiting the scope of the invention in any way, as many variations and equivalents that are encompassed by the present invention will become apparent to those skilled in the art upon reading the present disclosure.

Example 1: Preparation of Oral Formulations

Oral irinotecan tablet formulations were prepared with the compositions shown in Table 1 to Table 7. Compositions are given for irinotecan potency equivalent to 7.5 mg irinotecan base but could as well have been adjusted on every other irinotecan potencies by adjusting the tablet weights.

Oral Formulation P01:
Tablet composition is given in Table 1

TABLE 1

Composition of P01

| Ingredient | Function | Amount (mg) | Amount (%) |
| --- | --- | --- | --- |
| Irinotecan base | Active ingredient | 7.5 | 3.55 |
| Palmitic acid | Vehicle | 78.61 | 37.26 |
| Vitamin E Polyethylene Glycol Succinate | Vehicle/surfactant | 13.87 | 6.58 |
| Lactose monohydrate 200 mesh | Carrier | 66.67 | 31.60 |
| Butylated hydroxytoluene | Antioxidant | 0.02 | 0.01 |
| Microcrystalline cellulose | Binder/filler | 26.40 | 12.50 |
| Croscarmellose sodium | Disintegrant | 15.83 | 7.50 |
| Magnesium stearate | Lubricant | 2.11 | 1.00 |
| Total | | 210.98 | 100.0 |

Irinotecan base was dissolved in molten Palmitic acid and Vitamin E Polyethylene Glycol Succinate (75° C.), and granulated with Lactose monohydrate using Butylated hydroxytoluene as antioxidant. The granulate was mixed with Microcrystalline cellulose and Croscarmellose sodium for 10 minutes. At last, magnesium stearate was added and mixing was done for 30 seconds. The mixture was compressed into tablets with tablet weight 211 mg and hardness of 65 N.

Oral Formulation P02:
Tablet composition is given in Table 2.

TABLE 2

Composition of P02

| Ingredient | Function | Amount (mg) | Amount (%) |
| --- | --- | --- | --- |
| Irinotecan base | Active ingredient | 7.5 | 4.14 |
| Lactose, spray-dried | Filler | 128.77 | 71.14 |
| Microcrystalline cellulose | Binder/filler | 42.92 | 23.71 |
| Magnesium stearate | Lubricant | 1.81 | 1.00 |
| Total | | 181.00 | 100.0 |

Irinotecan base was mixed with Microcrystalline cellulose for 10 minutes. Lactose was added and mixing was repeated. At last, magnesium stearate was added and mixing was done for 30 seconds. The mixture was compressed into tablets with tablet weight 181 mg and hardness of 65 N.

Oral Formulation P03:
Tablet Composition is Given in Table 3.

TABLE 3

Composition of P03

| Ingredient | Function | Amount (mg) | Amount (%) |
| --- | --- | --- | --- |
| Irinotecan hydrochloride, 3H$_2$O | Active ingredient | 8.66 | 4.76 |
| Lactose, spray-dried | Filler | 128.64 | 70.68 |
| Microcrystalline cellulose | Binder/filler | 42.88 | 23.56 |
| Magnesium stearate | Lubricant | 1.82 | 1.00 |
| Total | | 182.00 | 100.0 |

Irinotecan hydrochloride was mixed with Microcrystalline Cellulose for 10 minutes. Lactose was added and mixing was repeated. At last, magnesium stearate was added and mixing was done for 30 seconds. The mixture was compressed into tablets with tablet weight 182 mg and hardness of 80 N.

Oral Formulation P04:

Tablet composition is given in

Table 4.

TABLE 4

Composition of P04

| Ingredient | Function | Amount (mg) | Amount (%) |
|---|---|---|---|
| Irinotecan hydrochloride, 3H$_2$O | Active ingredient | 8.66 | 4.14 |
| Polyethylene glycol 6000 | Vehicle | 54.17 | 25.92 |
| Poloxamer 188 | Vehicle/surfactant | 36.11 | 17.28 |
| Lactose 200 mesh | Carrier | 65.96 | 31.56 |
| Butylated hydroxytoluene | Antioxidant | 0.02 | 0.01 |
| Microcrystalline cellulose | Binder/filler | 26.33 | 12.60 |
| Croscarmellose sodium | Disintegrant | 15.68 | 7.50 |
| Magnesium stearate | Lubricant | 2.09 | 1.00 |
| Total | | 209.0 | 100.0 |

Irinotecan hydrochloride was dispersed in molten Polyethylene glycol 6000 and Poloxamer 188 (75° C.), and granulated with Lactose monohydrate using Butylated hydroxytoluene as antioxidant. The granulate was mixed with Microcrystalline cellulose and Croscarmellose sodium for 10 minutes. At last, magnesium stearate was added and mixing was done for 30 seconds. The mixture was compressed into tablets with tablet weight 209 mg and hardness of 52 N.

Oral Formulation P05:

Tablet composition is given in Table 5.

TABLE 5

Composition of P05

| Ingredient | Function | Amount (mg) | Amount (%) |
|---|---|---|---|
| Irinotecan hydrochloride, 3H$_2$O | Active ingredient | 8.66 | 4.14 |
| Polyethylene glycol 6000 | Vehicle | 76.74 | 36.72 |
| Vitamin E Polyethylene Glycol Succinate | Vehicle/surfactant | 13.54 | 6.48 |
| Lactose 200 mesh | Carrier | 65.96 | 31.56 |
| Butylated hydroxytoluene | Antioxidant | 0.02 | 0.01 |
| Microcrystalline cellulose | Binder/filler | 26.33 | 12.60 |
| Croscarmellose sodium | Disintegrant | 15.68 | 7.50 |
| Magnesium stearate | Lubricant | 2.09 | 1.00 |
| Total | | 209.0 | 100.0 |

Irinotecan hydrochloride was dispersed in molten Polyethylene glycol 6000 and Vitamin E Polyethylene Glycol Succinate (70° C.), and granulated with Lactose monohydrate using Butylated hydroxytoluene as antioxidant. The granulate was mixed with Microcrystalline cellulose and Croscarmellose sodium for 10 minutes. At last, magnesium stearate was added and mixing was done for 30 seconds. The mixture was compressed into tablets with tablet weight 209 mg and hardness of 50 N.

Oral Formulation P06:

Composition of solution is given in Table 7.

TABLE 6

Composition of P06

| Ingredient | Function | Amount (mg) | Amount (%) |
|---|---|---|---|
| Irinotecan hydrochloride, 3H$_2$O | Active ingredient | 8.66 | 4.14 |
| Lauroyl polyoxyl-32 glycerides | Vehicle/surfactant | 90.28 | 43.20 |
| Lactose 200 mesh | Carrier | 65.96 | 31.56 |
| Butylated hydroxytoluene | Antioxidant | 0.02 | 0.01 |
| Microcrystalline cellulose | Binder/filler | 26.33 | 12.60 |
| Croscarmellose sodium | Disintegrant | 15.68 | 7.50 |
| Magnesium stearate | Lubricant | 2.09 | 1.00 |
| Total | | 209.0 | 100.0 |

Irinotecan hydrochloride was dispersed in molten Lauroyl polyoxyl-32 glycerides (60° C.), and granulated with Lactose monohydrate using Butylated hydroxytoluene as antioxidant. The granulate was mixed with Microcrystalline cellulose and Croscarmellose sodium for 10 minutes. At last, magnesium stearate was added and mixing was done for 30 seconds. The mixture was compressed into tablets with tablet weight 209 mg and hardness of 50 N.

Granulation Processes

The stated compositions of granulates can be produced by different granulation processes to achieve the provided formulations, for instance high shear mixing, spray granulation, spray drying and hot melt extrusion.

Tablet formulations provided were all granulated by high shear mixing: The mixture of vehicles and surfactants was melted (at typically 75° C.) and butylated hydroxytoluene added. The active ingredient (irinotecan base or irinotecan hydrochlorid) was then added to the vehicle mixture and dissolved (irinotecan base) or dispersed (irinotecan hydrochloride). Lactose monohydrate was transferred to the high shear mixer and the molten active vehicle slowly poured upon the lactose monohydrate to form granules while cooling the mixer bowl by cold water in the jacket. The produced granulates were sieved through a rotating screen, size 2388.

Capsule formulations could be achieved from the above formulations by filling the produced granulates into hard shell capsules followed by enteric coating.

Powder formulations (granules) could be achieved from the above formulations by enteric coating of the produced granulates followed by filling into sachets.

Oral Formulation P07:

Composition of solution is given in Table 7.

TABLE 7

Composition of P07

| Ingredient | Function | Amount (mg) | Amount (%) |
|---|---|---|---|
| Irinotecan base | Active ingredient | 7.50 | 7.50 |
| Oleic acid | Vehicle | 77.08 | 77.08 |
| Vitamin E Polyethylene Glycol Succinate | Vehicle/surfactant | 15.40 | 15.40 |
| Butylated hydroxytoluene | Antioxidant | 0.02 | 0.02 |
| Total | | 100 mg | 100.0 |

Irinotecan base was dissolved in Oleic acid and molten Vitamin E Polyethylene Glycol Succinate (60° C.), and Butylated hydroxytoluene was added as antioxidant.

The solution was loaded into Gelatin capsules or loadable tablet cores.

Film Coating

Tablet formulations were film-coated with a sub-coating followed by en enteric coating. The purpose of the sub-coating was to enable better adhesion of the enteric coating. The composition of the sub-coating is provided in Table 8 (5% weight increase) and enteric coating in Table 9 (7% weight increase).

Film-coatings were performed in conventional coating equipment (fluid-bed) with the coating parameters recommended by the supplier of film formulations.

TABLE 8

Sub-coating

| Ingredient | Function | Amount (%) |
| --- | --- | --- |
| Opadry AMB OY-B-28920 | Film formulation | 15.0 |
| Purified water | Solvent | 85.0 |
| Total | | 100.0 |

TABLE 9

Enteric coating

| Ingredient | Function | Amount (%) |
| --- | --- | --- |
| Acryl EZE white | Film formulation | 20.0 |
| Dimethicone | Anti-sticking agent | 0.02 |
| Triethylcitrate | Plasticizer | 2.0 |
| Purified water | Solvent | 77.98 |
| Total | | 100.0 |

Example 2: Single Dose Pharmacokinetic Study in BAMA Pig

A single dose pharmacokinetic study was performed in BAMA pigs to study the pharmacokinetic properties of irinotecan after oral administration of two solid oral dosage forms. The study design was a randomized, balanced, parallel group design. Each formulation was tested in totally six BAMA pigs.

Two solid oral dosage forms named P01, P02 formulated with irinotcan base were tested. The composition of the formulations P01 and P02 were as described in Example 1.

One day prior to dosing the dogs were deprived of food from late afternoon by removing the feeding trough. The food was resumed at 8 hours post dose. Gastric stomach pH was measured prior to administration of the solid oral dosage forms.

Each animal received totally six (6) tablets of 7.5 mg irinotecan, i.e. 45 mg irinotecan in total per pig regardless of weight corresponding to a range of 2.5-2.9 mg/kg or 81.3-90.2 mg/m² of body surface area. An oral applicator was used for peroral (PO administration) and the tablet was put directly on the aditus laryngis of the dog to ensure that the tablets were not chewed but swallowed as whole tablets. The animals received 60 mL of water immediately following the tablet dosing to ensure the complete oral dosing.

Blood samples (approximately ~0.5 mL) are taken from each animal at each dosing occasion on 10 time points up to 24 hours after dosing (0 (pre-dose); 1; 1.5; 2; 3; 4; 6; 8; 12; 24 h). Samples will be placed in tubes containing EDTA (K2) and stored on an ice block until centrifuged at 4° C. to obtain plasma within 15 minutes of sample collection. All samples are stored at approximately −70° C. until bioanalysis were performed. Irinotecan and the active metabolite SN38 were both measured. At least two standard curves plus 6 QC samples (duplicate at each concentration) are applied during sample analysis for each run. The actual number of standard curves and QC samples depend on the amount of unknown sample.

The PK parameters were determined by non-compartmental model of non-compartmental analysis tool, Pharsight Phoenix WinNonlin® 6.2 software. The pharmacokinetic parameters calculated are i.e. total exposure, or area under the concentration-time curve (AUC0-inf, AUC0-t), Peak exposure (Cmax), Time to peak exposure (Tmax) and half-life (t½). The pharmacokinetic data are provided in the table 10 below.

TABLE 10

Pharmacokinetic parameters of Irinotecan (free base) after oral dose of Irinotecan at 45 mg/animal in fasted male BAMA pigs (N = 6)

| Treatment | PK parameters | | | | |
| --- | --- | --- | --- | --- | --- |
| | $T_{max}$ | $C_{max}$ | $t_{1/2}$ | $AUC_{0\text{-}last}$ | $AUC_{INF}$ |
| | | | Unit | | |
| | hr | ng/mL | hr | hr * ng/mL | hr * ng/mL |
| | PK parameters of Irinotecan | | | | |
| P01 | 5.00 | 127 | 10.9 | 1100 | 1238 |
| P02 | 17.0 | 29.8 | 12.3 | 260 | 483 |

Example 3: Single Dose Pharmacokinetic Study in Beagle Dogs

A single dose pharmacokinetic study was performed in Beagle dogs to study the pharmacokinetic properties of irinotecan after oral administration of solid oral dosage forms. The study design was a randomized, balanced, parallel group design and included twelve Beagle dogs. Each formulation was tested in totally four dogs.

Three solid oral dosage forms named P01, P04 and P05 and formulated with respectively irinotcan base (P01) and irinotecan, hydrochloride, trihydrate (P04 and P05) were tested. The composition of the formulations P01, P04 and P05 were as described in Example 1.

One day prior to dosing the dogs were deprived of food from late afternoon by removing the feeding trough. The food was resumed at 8 hours post dose. Pentagastrin was dosed via IM (6 µg/kg, 200 µg/mL in water) 30 min prior to administration of the solid oral dosage forms. Pentagastrin was administered to ensure low pH in the dog's stomach, which otherwise will not have an as low pH as in humans stomachs. Gastric pH was measured right before pentagastrin dosing and right before irinotecan dosing.

Each animal received totally four (4) tablets of 7.5 mg irinotecan, i.e. 30 mg irinotecan in total corresponding to a range of 3.1-3.6 mg/kg or 60.8-67.6 mg/m² (body surface area=0.1077*body weight^(⅔)). An oral applicator was used for peroral (PO administration) and the tablet was put directly on the aditus laryngis of the dog to ensure that the tablets were not chewed but swallowed as whole tablets. The animals received 100 mL of water immediately following the tablet dosing to ensure the complete oral dose was received.

The blood sampling procedure as well as time-points, bio-analysis and the calculation of PK parameters were determined as described in example 2 above.

The pharmacokinetic data obtained are provided in the table 11 below.

TABLE 11

Summary of major pharmacokinetic parameters of Irinotecan (free base) and two metabolites (SN-38 and SN-38 glucoronide (SN-38G) after oral dose of Irinotecan at 30 mg/animal in fasted male Beagle dogs (N = 6).

| | | | PK parameters | | |
|---|---|---|---|---|---|
| Treat-ment Group | Tmax hr | Cmax ng/mL | t½ hr | $AUC_{0-last}$ Unit hr * ng/mL | $AUC_{INF}$ hr * ng/mL | $AUC0$-last (metabolite)/ $AUC0$-last (parent) % |

| Treatment | Tmax | Cmax | t½ | $AUC_{0-last}$ | $AUC_{INF}$ | ratio |
|---|---|---|---|---|---|---|
| *PK parameters of Irinotecan* | | | | | | |
| P01 | 2.58 | 1073 | 3.28 | 5989 | 6038 | |
| P04 | 3.00 | 1216 | 3.27 | 8063 | 8138 | |
| P05 | 2.58 | 1240 | 4.39 | 6888 | 7139 | |
| *PK parameters of total SN-38 (sum of SN-38 + SN-38G)* | | | | | | |
| P01 | 2.58 | 7.47 | 7.20 | 32.4 | 75.5 | 0.560 |
| P04 | 4.67 | 9.67 | 8.27 | 71.7 | 132 | 0.913 |
| P05 | 3.83 | 9.97 | 6.41 | 66.9 | 113 | 0.963 |
| *PK parameters of SN-38* | | | | | | |
| P01 | 2.58 | 5.05 | 4.31 | 23.2 | 34.9 | 0.372 |

The coefficients of variations (CV %) for the tablet formulations P01, P04 and P05 were for $C_{max}$ 17.5%; 22.3% and 14.5%, respectively and were for $AUC_{0-last}$ 21.1%; 23.0% and 13.7%, respectively.

Example 4

The solid oral dosage form named P01 was tested in a Combined Pharmacokinetic and Repeat Dose Toxicity Study in beagle dogs. The study design was a 2-arm parallel group study comparing irinotecan IV infusion with oral administration of the P01 tablet Animals were observed daily for a period of 3 weeks corresponding to one treatment cycle.

Group 1 (n=4) received a single infusion over 60 min of Irinotecan "Accord" of 350 mg Irinotecan hydrochloride, trihydrate/m² corresponding to 303 mg of Irinotecan (as free base)/m². Group 2 (n=6) received one P01 tablet 12 mg/animal once daily for 14 days corresponding to 23.69-26.38 mg of Irinotecan (as free base)/m². Animals in Group 2 further received a daily intra muscular injection Pentagastrin (6 μg/kg) 30 min prior to the oral treatment with the Irinotecan tablet in order to mimic the human pH in the stomach during the dosing period.

Pharmacokinetic blood samples were taken at appropriate intervals during the first 24 post dosing on Day 1 for both groups and in addition on Day 5 and Day 14 for group 2 (P01 tablet). Data are shown in Table 12 and Table 13 below.

After administration of tablets (Group 2), the maximum plasma concentration was observed at the same time points (1.5 to 2 hours after dosing) for both Irinotecan and SN-38. The half-life of Irinotecan and SN-38 appeared at approximately 4 hours both after infusion and oral dosing. No or only a very modest accumulation of Irinotecan was observed after daily oral dosing for 14 days.

TABLE 12

Summary of average pharmacokinetic parameters after dosing with infusion of Irinotecan.

| D/BSA (mg/m²) | $T_{1/2}$ (hr) | C0 (ng/ml) | C0/D (ng/ml)/ (mg/m²) | $C_{max}$ (ng/ml) | $C_{max}$/D (ng/ml)/ (mg/m²) | $AUC_{last}$ (hr * ng/ml) | $AUC_{INF}$ (hr * ng/ml) | $AUC_{INF}$/D (hr * ng/ml)/ (mg/m²) | Cl (ml/hr/m²) | Vz (ml/m²) |
|---|---|---|---|---|---|---|---|---|---|---|
| 303 | 3.8 | 8837 | 29.2 | 8868 | 29.3 | 44573 | 45179 | 149 | 7217 | 40091 |

TABLE 13

Summary of average pharmacokinetic parameters after dosing with Irinotecan as tablets

| Day | D/BSA (mg/m²) | $T_{1/2}$ (hr) | $T_{max}$ (hr) | $C_{max}$ (ng/ml) | $C_{max}$/D (ng/ml)/ (mg/m²) | $AUC_{0\_24}$ (hr * ng/ml) | $AUC_{INF}$ (hr * ng/ml) | $AUC_{INF}$/D (hr * ng/ml)/ (mg/m²) | F | Ra |
|---|---|---|---|---|---|---|---|---|---|---|
| 1 | 25.0 | 4.2 | 1.8 | 197 | 7.9 | 625 | 632 | 25.3 | 0.17 | — |
| 5 | 25.0 | 4.4 | 1.7 | 221 | 8.9 | 726 | 738 | 29.6 | — | 1.18 |
| 14 | 24.9 | 3.0 | 1.8 | 228 | 9.2 | 831 | 832 | 34.1 | — | 1.45 |

The oral bioavailability of Irinotecan was calculated to 17%. The metabolite ratio of the conversion of SN-38 from the parent compound Irinotecan was higher after oral administration than infusion (0.37% and 0.27%, respectively). This indicates that a part of the conversion to SN-38 might have taken place before the drug reached systemic circulation, probably in the intestine.

Vomit and soft, watery or bloody/mucous faeces were observed in all four animals In connection with the infusion of animals in the Group 1. In Group 2 (P01 tablets) only a few incidences of soft, mucous or bloody/mucous faeces was recorded during the treatment period. Overall, animals gained weight over the duration of the study (from Day 1 to Day 22), however transient body weight loss considered related to the treatment with Irinotecan was recorded in some animals in both groups and mostly for the infusion treated animals.

TABLE 14

Development in animal weight from 21 days before treatment and until end of the 3 week treatment cycle.

| Day in study | IV infusion Mean body weight (kg) | P01 Tablets Mean body weight (kg) |
|---|---|---|
| Day −21 | 9.4 | 10.2 |
| Day −14 | 9.5 | 10.0 |
| Day −7 | 9.7 | 10.3 |
| Day −3 | 9.8 | 10.4 |
| Day 1 | 10.0 | 10.6 |
| Day 4 | 9.5 | 10.5 |
| Day 8 | 9.9 | 10.4 |
| Day 15 | 10.2 | 10.6 |
| Day 22 | 10.3 | 10.6 |

For both groups, test item related changes were observed in both haematology (red blood cells and white blood cells) and clinical chemistry parameters (electrolytes and creatinine) The effect on the white blood cell counts were most affected in animals treated with Irinotecan IV infusion (see Table 15). For animals treated with Irinotecan IV infusion several blood parameters were below the normal background especially for Day 4 and Day 8 but all returned to normal background at Day 22. For the Group 2 treated with P01 tablets all values were within normal background range throughout the period.

TABLE 15

Development in white blood cell count (WBC) and neutrophils from prior to treatment and until the end of the 3 week treatment cycle.

| | IV infusion | | P01 Tablets | |
|---|---|---|---|---|
| Day in study | WBC (10 × 9/L) | Neutrofils (10 × 9/L) | WBC (10 × 9/L) | Neutrofils (10 × 9/L) |
| Prior | 10.15 | 6.75 | 12.08 | 7.88 |
| Day 4 | 6.48 | 4.58 | 11.07 | 7.25 |
| Day 8 | 7.33 | 4.20 | 10.67 | 7.27 |
| Day 15 | 11.08 | 7.43 | 9.77 | 6.45 |
| Day 22 | 9.60 | 6.73 | 11.30 | 7.58 |

Example 5

Dissolution testing was performed on tablets from example 1. Dissolution was done using a dissolution system with paddle (USP2). The dissolution media A was 0.1 N HCl and dissolution media B was phosphate buffer pH 6 with 1% Sodium Dodecyl Sulfate (SLS). Dissolution media A was prepared by dissolving 41 ml 37% hydrochloride acid in 5 l de-ionized water. Dissolution media B was prepared by dissolving 136 g monobasic sodium phosphate in 20 l de-ionized water and adjusted to pH=6 with approx. 22 ml 10 N NaOH. Dissolution was conducted at 37° C. at 75 RPM. Samples were taken at regular intervals and filtrated through a 0.45 µm filter and the absorption at 359 nm was determined by UV spectrometry. The release of irinotecan relative to the release after 1 or 2 hours was calculated. The release of irinotecan over time is given in the table 16 and 17 below for the 2 dissolution systems.

TABLE 16

Dissolution of irinotecan formulations in dissolution media A (0.1N HCl). % irinotecan in tablet dissolved

| | 0 min | 120 min |
|---|---|---|
| P01 | 0 | 0 |
| P02 | 0 | 0 |
| P03 | 0 | na |
| P04 | 0 | 0 |
| P05 | 0 | 0 |

TABLE 17

Dissolution of irinotecan formulations in dissolution media B (phosphate buffer pH 6 with 1% SLS). % irinotecan in tablet dissolved

| | 0 min | 10 min | 15 min | 20 min | 30 min | 45 min | 60 min |
|---|---|---|---|---|---|---|---|
| P01 | 0 | na | 43 | na | 66 | 86 | 100 |
| P02 | 0 | 91 | 96 | 98 | 98 | 97 | 100 |
| P03 | 0 | 89 | 94 | 97 | 98 | 98 | 100 |
| P04 | 0 | na | 21 | na | 69 | 94 | 100 |
| P05 | 0 | na | 33 | na | 67 | 95 | 101 | na = not analyzed

Example 6

Dissolution testing was performed as average of double experiments on tablets from Example 1 as well as on the APIs used in form of the free base or the Irinotecan hydrochloride trihydrate. Dissolution was done using a dissolution system with paddle (USP2). The dissolution media was 900 ml 0.5M phosphate buffer adjusted to pH=8.0. The dissolution media was prepared by dissolving 8.8 g/liter dinatriumhydrogenphosphate dihydrate and adjusted to pH=8.0 with 30% HCl. Dissolution was conducted at 37° C. at 75 RPM. Samples were taken at regular intervals and the absorption at 359 nm was determined by UV spectrometry. The solubilized Irinotecan tablets (P01, P04, and P05) and the non-solubilized Irinotecan tablet (P03) from Example 1 was compared to the release of Irinotecan drug substance determined using the same dissolution conditions as for the tablets. The ratio between the release of Irinotecan from the tablet formulation relative to the release of Irinotecan from the corresponding drug substance alone as a measure of the relative solubilisation of the tablet formulation, is given in the table 18 below at regular time intervals up to 180 minutes. Solubilisation should be measured after the compositions have released all drug and an equilibrium obtained, that is between 60 minutes and 180 minutes.

TABLE 18

The solubilisation ratio for experimental tablets as function of dissolution time at pH = 8.0

|     | 15 min | 30 min | 60 min | 120 min | 180 min |
|-----|--------|--------|--------|---------|---------|
| PO3 | 1.6    | 1.2    | 1.3    | 1.3     | 1.3     |
| PO4 | 1.5    | 2.2    | 2.4    | 2.3     | 2.2     |
| PO5 | 1.2    | 1.8    | 2.3    | 2.2     | 2.1     |
| PO1 | 3.8    | 3.6    | 4.1    | 3.6     | 3.4     |

We claim:

1. A solid oral pharmaceutical composition comprising a compound of formula I

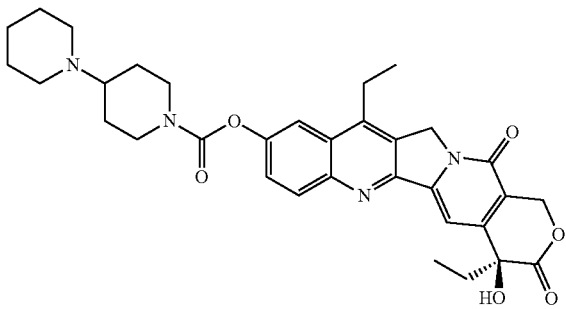 [SMILES: CCc1c2c(nc3ccc(OC(=O)N4CCC(N5CCCCC5)CC4)cc13)-c1cc3c(c(=O)n1C2)COC(=O)[C@]3(O)CC]

as a free base or a salt thereof, wherein the compound of formula (I) is solubilized in a mixture comprising (a) a vehicle, wherein the vehicle is selected from a saturated or unsaturated fatty acid of between 8-24 carbon atoms in length and a polyethylene glycol, having an average molecular weight of at least 3000 and (b) a water soluble non-ionic surfactant, wherein the water-soluble surfactant is selected from poloxamers, a tocopherol polyethylene glycol succinate derivative, lauroyl polyoxylglycerides, polysorbate 80, polyoxyl 40 hydrogenated castor oil, polyoxyl 35 castor oil, caprylocaproyl macrogolglycerides, polyoxyl 15 hydroxystearate and polyoxyethylene 10 oleyl ether, wherein the compound of formula I is in a solid core comprising about 0.5% to about 30% by weight of the compound of formula I.

2. The composition of claim 1 wherein the compound of formula I is the free base.

3. The composition of claim 1 wherein the compound of formula I is a hydrate.

4. The composition of claim 1 wherein the solid composition is coated with an enteric coating.

5. The composition of claim 4, wherein the enteric coating is insoluble in gastric juice and in intestinal juice below a predetermined pH in a human subject, but soluble in intestinal juice above the predetermined pH in the human subject.

6. The composition of claim 5, wherein the predetermined pH in the human subject is in a range from about 4.5 to about 7.

7. The composition of claim 1 wherein the vehicle comprises a saturated or unsaturated fatty acid of between 8-24 carbon atoms in length.

8. The composition of claim 1 wherein the vehicle comprises polyethylene glycol.

9. The composition of claim 1 comprising from about 2% to about 8% by weight of the compound of formula I.

10. The composition of claim 1 wherein the fatty acid is selected from linoleic acid (18:2), oleic acid (18:1), palmitic acid (16), linolenic acid (18:3), and stearic acid (18:0), and mixtures thereof, wherein the first number in the brackets refers to the number of carbon atoms in the fatty acid chain, and the second number refers to the degree of unsaturation.

11. The composition of claim 1 wherein the surfactant is Vitamin E polyethylene glycol succinate.

12. The composition of claim 1 wherein the vehicle a PEG having an average molecular weight of about 6000 present in an amount from about 20 to about 60 w/w %, based on the total weight of the pharmaceutical composition.

13. The composition of claim 1 wherein the surfactant is poloxamer.

14. The composition of claim 1, wherein the fatty acid contains between 16-18 carbon atoms.

15. A solid oral pharmaceutical composition comprising a compound of formula I

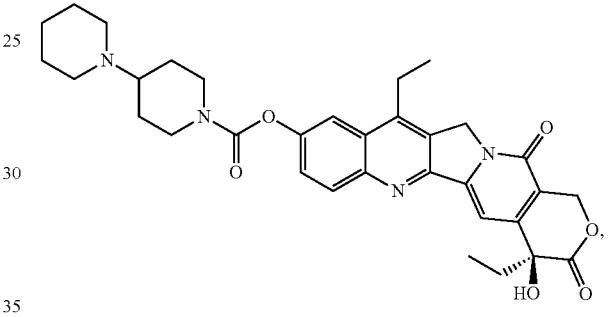

as a free base or a salt thereof, wherein the compound of formula (I) is solubilized in a mixture comprising a vehicle and a non-ionic surfactant, wherein the vehicle is a fatty acid of between 8-24 carbon atoms in length or PEG and the surfactant is a pegylated tocopherol, wherein the compound of formula I is in a solid core comprising about 0.5% to about 30% by weight of the compound of formula I and is present in an amount from about 1 to about 100 mg.

16. The composition of claim 15 wherein the mixture of the vehicle and surfactant is a mixture of a fatty acid of between 8-24 carbon atoms in length and pegylated tocopherol and, in a proportion on a weight/weight basis of from about 1:3 to about 10:1.

17. The composition of claim 16 wherein the fatty acid is palmitic acid and the pegylated tocopherol is vitamin E TPGS.

18. The composition of claim 15 wherein the mixture of the vehicle and the surfactant is a mixture of PEG and pegylated tocopherol.

19. The composition of claim 15 wherein the mixture of the vehicle and the surfactant is a mixture of PEG 6000 and vitamin E TPGS at a weight ratio from 6:4 to about 20:1.

* * * * *